Figure 1:
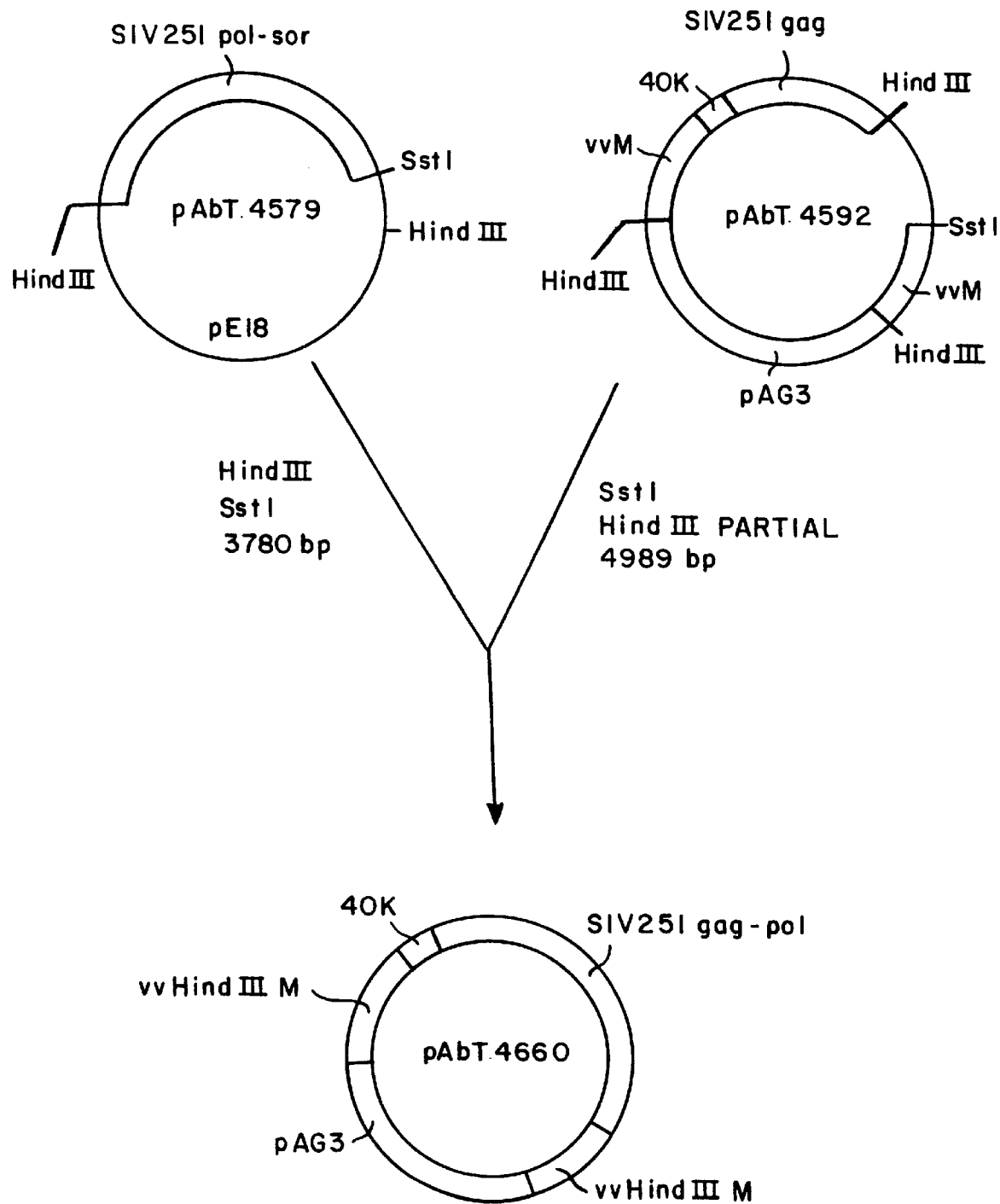

United States Patent [19]
Payne

[11] Patent Number: 5,858,726
[45] Date of Patent: Jan. 12, 1999

[54] SELF-ASSEMBLING REPLICATION DEFECTIVE HYBRID VIRUS PARTICLES

[75] Inventor: Lendon Payne, Arlington, Mass.

[73] Assignee: Therion Biologics, Cambridge, Mass.

[21] Appl. No.: 442,471

[22] Filed: May 16, 1995

Related U.S. Application Data

[62] Division of Ser. No. 17,124, Feb. 12, 1993, Pat. No. 5,420, 026, which is a continuation of Ser. No. 567,828, Aug. 15, 1990, abandoned, which is a continuation-in-part of Ser. No. 567,828, Aug. 15, 1990, abandoned.

[51] Int. Cl.$^6$ .......................... C12P 21/04; C12N 15/00; A61K 39/12
[52] U.S. Cl. .................. 435/69.7; 435/172.3; 424/199.1
[58] Field of Search ................. 435/69.7, 172.3; 424/199.1

[56] References Cited

U.S. PATENT DOCUMENTS

| | | | |
|---|---|---|---|
| 4,603,112 | 7/1986 | Paoletti et al. | 435/172.1 |
| 5,420,026 | 5/1995 | Payne | 435/172.3 |

FOREIGN PATENT DOCUMENTS

| | | |
|---|---|---|
| 0 175 261 | 3/1986 | European Pat. Off. . |
| 0 421 635 | 4/1991 | European Pat. Off. . |

OTHER PUBLICATIONS

Zavada, et al. J. Gen Virol., 63:15–24 (1982).
Lukashevich and Zavada, Acta Virolgica (1982).
Wilson, et al., J. Virol, 63:2374–2378 (1989).
Wills, et al., Nature, 340:323–324 (1989).
Zhu, et al., J. Acquired Immune Deficiency Syndrome, 3:215–219 (1990).
Shioda, et al., Virology, 175:139–148 (1990).
Haffar, et al., J. Virology, 64:2653–2659 (1990).
Karacostas, et al., Proc. Natl. Acad. Sci. USA, 86:8964–8967 (1989).
Delchambre, et al., The EMBO J., 8:2653–2660 (1989).
Rautmann, et al., AIDS Res. Hum. Retroviruses, 5:147–157 (1989).
Gowda, et al., J. Gen Virol., 63:1451–1454 (1989).
Mazzara, et al., "Modern Approached to Vaccines," Cold Spring Harbor Laboratory, New York (1987).
Smith, etal., J. Virol., 64:2743–2750 (1990).
Gheysen, D., et al., Cell 59:103 (1989).

Primary Examiner—Ponnathapura Achutamurthy
Assistant Examiner—Hankyel T. Park
Attorney, Agent, or Firm—Ronald I. Eisenstein; David S. Resnick; Dike, Bronstein, Roberts & Cushman, LLP

[57] ABSTRACT

The invention pertains to self-assembled replication defective hybrid virus-like particles having capsid and membrane glycoproteins from at least two different virus types and method of making same. Recombinant viral vectors as well as the viral particles can be used as immunogens and drug delivery vehicles.

7 Claims, 3 Drawing Sheets

SELF-ASSEMBLING REPLICATION DEFECTIVE HYBRID VIRUS PARTICLES

This is a divisional of copending application Ser. No. 08/017,124 filed on Feb. 12, 1993 Pat No. 5,420,026 International Application PCT/US91/05650 filed on Aug. 8, 1991 and which designated the U.S. which was a continuation in part of U.S. application Ser. No. 07/567,828 filed Aug. 15, 1990 abandoned.

BACKGROUND OF THE INVENTION

Vaccination has played a key role in the control of viral diseases during the past 30 years. Vaccination is based on a simple principle of immunity: once exposed to an infectious agent, an animal mounts an immune defense that provides lifelong protection against disease caused by the same agent. The goal of vaccination is to induce the animal to mount the defense prior to infection. Conventionally, this has been accomplished through the use of live attenuated or whole inactivated forms of the virus as immunogens. The success of these approaches depends on the presentation of native antigen which elicits the complete range of immune responses obtained in natural infection.

Despite their considerable success, conventional vaccine methodologies are subject to a number of potential limitations. Insufficiently inactivated vaccines may cause the disease they are designed to prevent. Attenuated strains can mutate to become more virulent or non-immunogenic. Viruses that can establish latency, such as the herpesviruses, are of particular concern as it is not known whether there are any long-term negative consequences of latent infection by attenuated strains. Finally, there are no efficient means of growing many types of viruses.

Recent advances in recombinant DNA technology offer the potential for developing vaccines based on the use of defined antigens as immunogens, rather than the intact infectious agent. These include peptide vaccines, consisting of chemically synthesized, immunoreactive epitopes; subunit vaccines, produced by expression of viral proteins in recombinant heterologous cells; and the use of live viral vectors for the presentation of one or more defined antigens.

Both peptide and subunit vaccines are subject to a number of potential limitations. A major problem is the difficulty of ensuring that the conformation of the engineered proteins mimics that of the antigens in their natural environment. Suitable adjuvants and, in the case of peptides, carrier proteins, must be used to boost the immune response. In addition these vaccines elicit primarily humoral responses, and thus may fail to evoke effective immunity. Subunit vaccines are often ineffective for diseases in which whole inactivated virus can be demonstrated to provide protection. For example, canine parvovirus subunits fail to elicit virus-neutralizing antibodies in rabbits (Smith and Halling, Gene, 29:263–269 (1984)), although protective inactivated vaccines are available.

As an alternative to recombinant-produced subunit vaccines comprising a purified polypeptide, it may be possible to develop non-infectious, subunit-like vaccines that consist of viral capsid proteins assembled into virus-like structures. Such non-replicating, virus-like particles would have many of the immunologic advantages of inactivated vaccines combined with the safety features of subunit vaccines. Several researchers have reported the development of eukaryotic systems for the expression of foreign viral capsid proteins, and the self assembly of these proteins into virus-like particles. For example, co-expression of canine parvovirus (CPV) capsid proteins VP1 and VP2 in murine cells transformed with a bovine papilloma virus/CPV recombinant plasmid resulted in the formation of self-assembling particles that resembled, biochemically and immunologically, authentic CPV virions (Mazzara, et al., *Modern Approaches to Vaccine,* Cold Spring Harbor Laboratory, N.Y., R. M. Chanock and R. A. Lerner, eds. pp. 419–424 (1986); Mazzara, et al., PCT Application No. WO88/02026, published Mar. 24, 1988). When used to vaccinate susceptible dogs, these empty capsids elicited immune responses capable of protecting against CPV challenge. In another example, it has been shown that the expression of HIV or SIV gag precursor polypeptide in insect cells using the baculovirus expression system results in the formation of immature, retroviral-like particles that are secreted into the culture medium of infected cells (Gheysen, et al., *Cell,* 59:103–112 (1989); Delchambre, et al., *EMBO J.,* 8:2653–2660 (1989)). In mammalian cells, HIV-like particles that contained core polypeptides as well as reverse transcriptase were produced after transient expression of the HIV gag-pol genes using an SV40 late replacement vector (Smith, et al., *J. Virol.,* 64:2653–2659 (1990)).

Recombinant vaccinia viruses that express at least the HIV gag gene have also been shown to give rise to the production of retroviral-like particles upon infection of appropriate host cells (Karacostas, et al., *Proc. Natl. Acad. Sci.* USA, 86:8964–8967 (1989); Shiota and Shibuta, *Virology,* 175:139–148 (1990)). The coexpression in recombinant vaccinia-infected cells of gag polypeptides with the HIV envelope glycoproteins resulted in the formation of HIV-like particles that comprised an enveloped core structure containing, embedded in the envelope, the HIV envelope glycoproteins. The coexpression of gag and env genes in infected cells could be achieved by co-infecting the cells with two different recombinant vaccinia viruses, one expressing env and one expressing gag-pol (Haffar, et al., *J. Virol.,* 64:2653–2659 (1990)), or by infecting the cells with a single recombinant that expressed both env and gag-pol (Mazzara, et al., U.S. patent application Ser. Nos. 07/360,027 and 07/540,109).

The ability to produce particles containing viral envelope glycoproteins has important implications for vaccine development. Viral envelope glycoproteins, which are located in the outer lipid membrane of enveloped viruses (such as herpesviruses, retroviruses, togaviruses, rhabdoviruses, paramyxoviruses, orthomyxoviruses and coronaviruses) are often the major immunogenic determinants of the virus. In the case of HIV, for example, the envelope glycoprotein gp120 contains the key epitopes that elicit virus-neutralizing antibody responses (Arthur, L. A., et al., *Proc. Natl. Acad. Sci.* USA, 84:8583–8587 (1987)). Similarly, the herpes simplex virus glycoprotein gB and the rabies glycoprotein both elicit virus-neutralizing antibody responses and, in addition, have been shown to protect against challenge with the cognate pathogens in the absence of other viral proteins (Paoletti, et al., *Proc. Natl. Acad. Sci.* USA, 81:193–197 (1984); Wiktor, et al., *Proc. Natl. Acad. Sci.* USA, 81:7194–7198 (1984)).

Unfortunately, there are many viruses for which heterologous expression of self-assembling viral capsids may not prove feasible. Formation of herpesviruses capsids, for example, would require the expression of more genes than can be practically accommodated in available expression vectors. The mechanism of particle assembly for a number of other viruses, such as the helical RNA viruses, makes self assembly of virus-like particles from a heterologous expression system problematic. Nonetheless, it would be useful to be able to produce non-infectious, self-assembling virus-like particles containing membrane glycoproteins from any enveloped virus.

Envelope glycoproteins from viruses of different families can be incorporated at low frequency into heterologous virus particles by the biological phenomenon known as pseudotyping or phenotypic mixing. In co-infection experiments, the genome of one virus species can be demonstrated to be physically associated with glycoproteins from the other species. In a review of the literature on this phenomenon, Zavada, (*J. Gen. Virol.*, 63:15–24 (1982)) cites examples of pseudotyping between, for example, retroviruses and togaviruses, rhabdoviruses, paramyxoviruses or herpesviruses. For pseudotyping to occur, the two viruses must have compatible life cycles, i.e., neither must interfere with the replication of the other. Recently, Zhu, et al., (*J. Acquired Immune Deficiency Syndromes*, 3:215–219 (1990)) described phenotypic mixing between HIV and vesicular stomatitis virus or herpes simplex virus.

SUMMARY OF THE INVENTION

This invention pertains to self-assembling, replication defective, hybrid virus-like particles. These particles, which contain polypeptides or portions of polypeptides from at least two different viral species, comprise assembled capsid polypeptides from one virus species surrounded by a membrane containing at least a portion of one or more viral envelope glycoproteins from one or more different virus species. The particles are produced using recombinant DNA viruses that express: (1) heterologous genes encoding virus capsid proteins and (2) a homologous or heterologous gene encoding an envelope glycoprotein. The capsid proteins and the envelope glycoprotein may be encoded in the same recombinant virus; in this case, infection of suitable host cells with the recombinant virus will result in the production of hybrid virus-like particles containing the encoded heterologous capsid proteins and the envelope glycoprotein. Alternatively, the capsid proteins and the envelope glycoprotein may be encoded in two or more different carrier viruses of the same species. In this case, hybrid virus-like particles are produced by co-infection of suitable host cells with the carrier virus.

This invention also pertains to the recombinant viruses expressing the proteins that comprise the particle and to the intermediate DNA vectors that recombine with the parent virus in vivo or in vitro to produce the recombinant virus. In addition, this invention pertains to methods of producing non-replicating, self-assembling hybrid virus particles and methods of using the particles as a biopharmaceutical in an appropriate formulation or using the recombinant virus expressing the particles as a delivery vehicle.

The hybrid virus-like particles and/or the virus capable of expressing the particles can be used as a vaccine against the correlate heterologous pathogens. The particles may contain, for example, capsid polypeptides from retroviruses (such as HIV, SIV, feline immunodeficiency virus (FIV), murine retroviruses, equine infectious anemia, visna virus and other retroviruses) or from other enveloped viruses in association with envelope glycoproteins from herpesviruses, retroviruses, togaviruses, rhabdoviruses, paramyxoviruses, orthomyxoviruses or coronaviruses. These particles can be used alone as immunogens or used in combination with other immunogens for vaccination against pathogenic viruses or for therapeutic purposes such as enhancing immune responses in an infected individual. The hybrid virus-like particles of this invention can also be used for targeted delivery of therapeutic agents, such as cytotoxic drugs or nucleic acids to specific cell types.

BRIEF DESCRIPTION OF THE FIGURES

FIG. 1 shows the construction of plasmid pAbT4660 which contains the entire SIV gag-pol region under the transcriptional control of the vaccinia 40K promoter.

FIG. 2 shows the construction of plasmid pAbT4602 which contains the pseudorabies virus gIII gene under the transcriptional control of the vaccinia 40K promoter.

FIG. 3 shows the construction of plasmid pAbT1527 which contains the gD gene of Herpes Simplex Virus Type 2.

DETAILED DESCRIPTION OF THE INVENTION

This invention pertains to self-assembling, replication defective, hybrid virus-like particles. The virus particles are hybrids in that they contain polypeptides from at least two different viral species. The invention is designed to take advantage of the phenomenon of pseudotyping to achieve assembly of the heterologous polypeptides into novel hybrid virus particles. The phenomenon of pseudotyping has been previously described in a review by Zavada, *J. Gen. Virol.,* 63:15–24 (1982).

Preferably, hybrid virus-like particles will contain retroviral capsid polypeptides, e.g., capsid polypeptides from lentiviruses, such as HIV, SIV, FIV, equine infectious anemia, visna virus, or from other retroviruses such as murine leukemia virus. The particles will also contain envelope glycoproteins from a different viral species. Such other viruses can be DNA or RNA viruses. The particles may further contain other desirable polypeptides appropriately linked to a viral envelope glycoprotein. The viral particles can have substantially little or no RNA packaged within the particle; or they can contain specific RNA for delivery of heterologous genes to a targeted cell. Methods for producing such viral particles have been described in U.S. application Ser. No. 07/540,109, filed Jun. 19, 1990, the teachings of which are incorporated herein by reference.

The method of producing hybrid virus-like particles, recombinant viruses expressing these particles, and uses therefor will be discussed in detail below and in the Examples section.

1. Genes Encoding Viral Capsid Polypeptides

Genes encoding viral polypeptides capable of self assembly into defective, nonself-propagating hybrid viral particles can be obtained from the genomic DNA of a DNA virus or the genomic cDNA of an RNA virus or from available subgenomic clones containing the genes. These genes will include those encoding viral capsid proteins (i.e., proteins that comprise the viral protein shell). Additional viral genes may also be required for capsid protein maturation and particle self-assembly. These may encode, for example, viral proteases responsible for processing of capsid protein.

One virus genus from which genes encoding self-assembling capsid proteins can be isolated is the lentiviruses, of which HIV is an example. The HIV gag protein is synthesized as a precursor polypeptide that is subsequently processed, by a viral protease, into the mature capsid polypeptides. However, the gag precursor polypeptide can self-assemble into virus-like particles in the absence of protein processing. Gheysen, et al., *Cell,* 59:103 (1989); Delchambre, et al., The *EMBO J.,* 8:2653–2660 (1989). HIV capsids are surrounded by a loose membranous envelope that contains the viral glycoproteins. In the native virus these are encoded by the HIV env gene.

2. Envelope Proteins

In order to create hybrid, non-self-propagating particles, part or all of the gene(s) for one or more envelope glycoproteins from a virus other than that used as the source of capsid genes are required.

Genes encoding envelope glycoproteins can be isolated from any of a large number of diverse, enveloped viruses. These viruses can be of either the DNA or RNA classes. Examples of enveloped viruses include herpesviruses, retroviruses, togaviruses, rhabdoviruses, paramyxoviruses, orthomyxoviruses and coronaviruses. Envelope glycoproteins are typically characterized by distinct intracellular, extracellular and transmembrane regions. An enveloped virus may express one or more envelope glycoproteins, which are often the major immunogenic determinants of the virus. Viral envelope glycoproteins may also be responsible for targeting specific cell surface receptors for virus adsorption and penetration into cells.

3. Parent Viruses

A number of viruses, including retroviruses for example, HIV, SIV, FIV, equine infectious anemia, and visna virus, adenoviruses, herpesviruses and pox viruses, have been developed as live viral vectors for the expression of heterologous antigens. Cepko, et al., *Cell,* 37:1053–1062 (1984); Morin, et al., *Proc. Natl. Acad. Sci.* USA, 84:4626–4630 (1987); Lowe, et al., *Proc. Natl. Acad. Sci.* USA, 84:3896–3900 (1987); Panicali & Paoletti, *Proc. Natl. Acad. Sci.* USA, 79:4927–4931 (1982); Mackett, et al., *Proc. Natl. Acad. Sci.* USA, 79:7415–7419 (1982). The examples given illustrate the use of the pox virus family. The preferred pox virus is vaccinia virus, a relatively benign virus which has been used for years as a vaccine against smallpox. Vaccinia virus has been developed as an infectious eukaryotic cloning vector (Paoletti and Panicali, U.S. Pat. No. 4,603,112) and recombinant vaccinia virus has been used successfully as a vaccine in several experimental systems. The virus is considered nononcogenic, has a well-characterized genome, and can carry large amounts of foreign DNA without loss of infectivity. Mackett, M. and G. L. Smith, *J. Gen. Virol.,* 67:2067 (1986). Another preferred pox virus is fowl pox virus, a pathogen of poultry. This virus has also been developed into a eukaryotic cloning vector. Boyle, et al., PCT Applications WO88/02022 published Sep. 22, 1987 and WO89/07644 published Aug. 24, 1989; Yanagida, et al., EP284416 published Sep. 28, 1988; PCT Application WO90/02191, published Mar. 8, 1991.

4. DNA Vectors for In Vivo Recombination with a Parent Virus

According to the method of this invention, viral genes that code for polypeptides capable of assembly into replication defective, hybrid viral particles are inserted into the genome of at least one parent virus in such a manner as to allow them to be expressed by that virus along with the expression of the normal complement of parent virus proteins. This can be accomplished by first constructing a DNA donor vector for in vivo recombination with a parent virus.

In general, the DNA donor vector contains the following elements:

(a) a prokaryotic origin of replication, so that the vector can be amplified in a prokaryotic host;

(b) a gene encoding a marker which allows selection of prokaryotic host cells that contain the vector (e.g., a gene encoding antibiotic resistance);

(c) heterologous genes from at least two different viruses each gene located adjacent to a transcriptional promoter (e.g., the vaccinia 7.5K, 30K, 40K, 11K or BamF promoters or modified versions of these promoters) capable of directing the expression of adjacent genes; and (d) DNA sequences homologous to the region of the parent virus genome where the foreign gene(s) will be inserted, flanking the construct of element c (e.g., the vaccinia TK or HindIII M sequences).

Methods for constructing donor plasmid for the introduction of multiple foreign genes into pox virus are described in EP 0261940, published Mar. 30, 1988, entitled "Pseudorabies Vaccine," the techniques of which are incorporated herein by reference. In general, all viral DNA fragments for construction of the donor vector, including fragments containing transcriptional promoters and fragments containing sequences homologous to the region of the parent virus genome into which foreign genes are to be inserted, can be obtained from genomic DNA or cloned DNA fragments.

The donor vector preferably contains an additional gene which encodes a selectable marker under control of a separate promoter which will allow identification of recombinant viruses containing inserted foreign DNA. Several types of marker genes can be used to permit the identification and isolation of recombinant viruses. These include genes that encode antibiotic or chemical resistance (e.g., see Spyropoulos, et al., *J. Virol.,* 62:1046 (1988); Falkner and Moss, *J. Virol.,* 62:1849 (1988); Franke, et al., *Mol. Cell. Biol.,* 5:1918 (1985)), as well as genes, such as the *E. coli* lacZ gene, that permit identification of recombinant viral plaques by calorimetric assay. (Panicali, et al., *Gene,* 47:193–199 (1986)).

A method for the selection of recombinant vaccinia viruses relies upon a single vaccinia-encoded function, namely the 29K host-range gene product. Gillard, et al., *Proc. Natl. Acad. Sci.* USA, 83:5573 (1986). This method was described in PCT Application No. WO89/12103, published Dec. 18, 1989, entitled "Methods of Selecting for Recombinant Pox Viruses," the teachings of which are incorporated herein by reference.

5. Integration of Foreign DNA Sequences into the Viral Genome and Isolation of Recombinants Homologous recombination between donor plasmid DNA and viral DNA in an infected cell results in the formation of recombinant viruses that incorporate the desired elements. Appropriate host cells for in vivo recombination are generally eukaryotic cells that can be infected by the virus and transfected by the plasmid vector. Examples of such cells suitable for use with a pox virus are chick embryo fibroblasts, RK13 (rabbit) cells, HuTK143 (human) cells, and CV-1 and BSC-40 (both monkey kidney) cells. Infection of cells with pox virus and transfection of these cells with plasmid vectors is accomplished by techniques standard in the art (Panicali and Paoletti, U.S. Pat. No. 4,603,112).

Following in vivo recombination, recombinant viral progeny can be identified by one of several techniques. For example, if the DNA donor vector is designed to insert foreign genes into the parent virus thymidine kinase (TK) gene, viruses containing integrated DNA will be $TK^-$ and can be selected on this basis (Mackett, et al., *Proc. Natl. Acad. Sci.* USA, 79:7415 (1982)). Alternatively, co-integration of a gene encoding a marker or indicator gene with the foreign gene(s) of interest, as described above, can be used to identify recombinant progeny. One preferred indicator gene is the *E. coli* lacZ gene: recombinant viruses expressing β-galactosidase can be selected using chromogenic substrate for the enzyme (Panicali, et al., *Gene,* 47:193 (1986)). A second preferred indicator gene for use with recombinant vaccinia virus is the vaccinia 29K gene: recombinant viruses that express the wild type 29K gene-encoded function can be selected by growth on RK-13 cells. Another method by which recombinant viruses containing genes of interest can be identified is by an in situ enzyme based immunoassay performed on virus plaques which detects foreign protein expressed by vaccinia-infected cells.

As described more fully in the Examples, donor plasmids containing SIV or pseudorabies virus genes could be recombined into vaccinia viruses either at the HindIII M region or TK region. Using either insertion site, recombinant viruses can be selected as described above.

6. Characterizating the Viral Antigens Expressed by Recombinant Viruses

Once a recombinant virus has been identified, a variety of methods can be used to assay the expression of the polypeptide encoded by the inserted gene. These methods include black plaque assay (an in situ enzyme immunoassay performed on viral plaques), Western blot analysis, radioimmunoprecipitation (RIPA), and enzyme immunoassay (EIA). Antibodies to antigens expressed by viral pathogens are either readily available, or may be made according to methods known in the art. For example, for simian immunodeficiency virus, the antibodies can be sera from macaques infected with SIV.

7. Viral Particle Formation

Expression analysis described in the preceding section can be used to confirm the synthesis of the polypeptides encoded by inserted heterologous viral genes, but does not address the question of whether these polypeptides self-assemble, in vivo or in vitro, into replication defective viral particles. This can readily be determined empirically based upon the present disclosure.

Cells can be infected in vitro with one DNA carrier virus expressing a capsid polypeptide, for example, retroviral gag or gag-pol genes, and a second carrier virus expressing an envelope glycoprotein gene. Preferably, the cell is co-infected. More preferably, it is co-infected with the same carrier DNA virus. Alternatively, a single carrier virus that expresses both a capsid polypeptide gene and an envelope gene can be used.

For self assembly to occur, the capsid and env gene products need to be expressed at about the same time. This can readily be accomplished by a variety of methods well known to the person of ordinary skill in the art. For example, one can use a viral vector containing the heterologous env and capsid genes. Alternatively, one can co-infect a cell with two viral vectors where one expresses the heterologous capsid genes and a second viral vector containing a gene expressing an env glycoprotein. Preferably, the viral vectors would have a similar life cycle so that the capsid and env gene products are expressed at about the same time. Still more preferably, the viral vectors would correspond to the same viral genome. In another embodiment, one can have the env and or capsid gene under the control of an inducible promoter, see for example, Haynes, et al., PCT Application No. WO91/05865, published May 2, 1991. Thus, one can turn these genes "on" at about the same time, so that one can obtain the expression of their gene products at about the same time, thereby resulting in self-assembly of the particle. In another embodiment, only one of the genes needs to be under the control of an inducible promoter, for example, the human metallothionein IIa promoter. One can then transform a cell containing this viral gene with the other viral vector, induce the gene already in the cell to express the capsid gene or the env gene under its control so that its expression coincides with that of the gene on the vector being used to transform the cell.

In order to characterize the defective hybrid viral particles produced by recombinant viruses expressing heterologous viral polypeptides, cells can be infected with the recombinant virus(es) in the presence of radiolabeled amino acid. High speed centrifugation can then be used to sediment particles from the culture medium. The pellet resulting from centrifugation of the culture medium can be resuspended and both the pellet and the supernatant can be immunoprecipitated with appropriate antisera to analyze the polypeptides present in each fraction. For example, in the case of recombinants expressing SIV capsid polypeptides, macaque anti-SIV antisera can be used for the analysis of capsid polypeptides. A second antibody, specific for the glycoprotein, would be used to detect the presence of the glycoprotein in the particle preparation.

To further characterize the material in the pellet resulting from centrifugation of the culture medium, the pellet can be resuspended and analyzed by centrifugation through a sucrose density gradient. The gradient can then be fractionated and the fractions immunoprecipitated with the appropriate antisera. These experiments show whether the pellet contains capsid material banding at the density expected for defective viral particles, and whether the envelope glycoprotein is specifically associated with the defective viral particles banding at this density.

Alternatively, formation of hybrid particles can be demonstrated using electron microscopy. After infection of appropriate host cells with the recombinant virus(es) expressing capsid and envelope glycoprotein genes, particles can be harvested from the culture medium by high speed centrifugation as described above. The presence of envelope glycoproteins on the surface of the particles can be demonstrated by immunogold staining, using a monoclonal antibody directed against the envelope glycoprotein, followed by electron microscopic examination.

8. Vaccines

Live recombinant viral vectors that express heterologous viral antigens capable of self-assembly into replication defective hybrid virus particles can be used to vaccinate humans or animals susceptible to infection if the viral vector used to express the heterologous defective virus particles infects but does not cause significant disease in the vaccinated host. Examples of such benign viral vectors include certain pox viruses, adenoviruses, and herpesviruses.

Alternatively, the defective hybrid virus particles produced by these recombinant vector viruses can be isolated from the culture medium of cells infected in vitro with the recombinant vector viruses. The purified particles used for vaccination of individuals susceptible to viral infection will authentically present envelope glycoproteins to the host immune system, but will not contain infectious viral genetic material. Consequently, they offer the advantage of conventional killed virus vaccine preparations, yet circumvent the major drawbacks to the use of killed virus as a vaccine for the prevention of infection. These include the danger of incomplete inactivation of killed virus preparations and, in the case of certain viruses, such as retroviruses, the reluctance to introduce a complete viral genome (the HIV genome, for example) into seronegative individuals.

Vaccine compositions utilizing these replication defective hybrid virus particles would generally comprise an immunizing amount of the viral particles in a pharmaceutically acceptable vehicle. The vaccines would be administered in a manner compatible with the dosage formulation, and in such amount as would be therapeutically effective and immunogenic.

Finally, the purified particles may be used in combination with live recombinant viruses as part of a total vaccination protocol, either as the primary immunizing agent, to be followed by vaccination with live recombinant virus, or to boost the total immune response after primary vaccination with live recombinant virus.

9. Therapeutic Use of Recombinant Viruses Expressing Viral Antigens Capable of Assembling into Defective Hybrid Viral Particles: Therapeutic Use of Defective Hybrid Viral Particles Produced by These Recombinant Viruses Even if immunization can not protect against initial infection, immunization of a previously infected individual with the hybrid particles might, for certain viruses, sufficiently boost immunity to protect against the onset of disease. This is, for example, how rabies vaccine is used therapeutically. Alternatively, for viruses that establish latency, immunization of an infected individual might prolong the latency period of that virus within the individual. (Salk, *Nature,* 327:473–476 (1987)). This may be particularly important in the case of viral infections characterized by long latency periods, such as HIV or herpesvirus infections.

The defective hybrid viral particles of this invention can also be used to deliver heterologous genes (e.g., antisense genes, genes encoding toxins, genes encoding an immunogen) to a targeted cell. Methods for producing such viral particles have been described in U.S. patent application Ser. No. 07/540,109, filed Jun. 19, 1990, the teachings of which are incorporated herein by reference. Hybrid viral particles could be used to deliver mRNAs that are directly translated in the target cell into the encoded protein product. Alternatively, specific RNA packaged within hybrid retroviral particles that contain active reverse transcriptase and other pol-encoded functions could be delivered to the targeted cells and reverse transcribed into DNA. This DNA could then integrate into the host genome, and the encoded genes would be expressed by host transcription/translation machinery. These approaches could be used to deliver genes encoding products toxic to the targeted cells (e.g., virally infected cells). In another application, particles containing RNA encoding heterologous genes could be administered to an individual in order to elicit immune responses to the encoded gene products.

10. Therapeutic Use of Defective Hybrid Virus Particles as Agents for Targeted Drug Delivery Defective, nonself-propagating virus particles can also be used to deliver certain drugs (e.g., cytotoxic drugs, antiviral agents, nucleic acids) to virus receptor-bearing cells. Such drugs may be coupled, by techniques known in the art, to the outer surface of the virus particle, or incorporated within, and delivered with high specificity to target cells. For example, cytotoxic drugs may be coupled to defective HIV particles and delivered with a high degree of specificity to $CD4^+$ T cells, since the HIV envelope glycoprotein present on these particles bind specifically and with high affinity to the CD4 molecule.

Specific targeting of therapeutic agents can be achieved by selecting as the heterologous glycoprotein one with a tropism for surface receptors on specific cell types. For example, hybrid particles containing herpesvirus glycoproteins might be used to target cells of the nervous system, whereas hybrid particles containing the hepatitis B surface antigen would target hepatic cells.

The invention will be further illustrated by the following examples:

EXAMPLES

General Procedures

Cells and Virus

*E. coli* strain MC1061 (Casadaban and Cohen, *J. Mol. Biol.,* 138:179 (1980)) was used as the host for the growth of all plasmids. The monkey kidney cell line BSC-40 (Brockman and Nathans, *Proc. Natl. Acad. Sci.* USA, 71:942 (1974)) and the rabbit kidney cell line RK-13 (ATCC No. CCL37; Beale, et al., *Lancet,* 2:640 (1963)) were used for vaccinia infections and transfections. Cells were propagated in Dulbecco modified Eagles Medium (DME, Gibco, Grand Island, N.Y.) supplemented with 5% fetal calf serum (FCS).

A 29K– lacZ+ strain vAbT33 (see U.S. patent application Ser. No. 205,189, filed Jun. 10, 1988, the teachings of which are incorporated herein by reference) was used as the parental virus for in vivo recombination. Viral infection, transfections, plaque purification and virus amplification were performed essentially as described (Spyropoulos, et al., *J. Virol.,* 62:1046 (1988)).

Molecular Cloning Procedures

Restriction enzyme digestions, purification of DNA fragments and plasmids, treatment of DNA with Klenow, T4 DNA polymerase, calf intestinal alkaline phosphatase, T4 DNA ligase, or linkers and transformation of *E. coli* were performed essentially as described (Maniatis, et al., *Molecular Cloning: A Laboratory Manual,* Cold Spring Harbor Laboratory, Cold Spring Harbor, N.Y., 1982, the teachings of which are incorporated herein by reference). Restriction enzymes were obtained from New England Biolabs or Boehringer-Mannheim. The large fragment of DNA polymerase (Klenow) was obtained from United States Biochemical Corporation, T4 DNA polymerase was obtained from New England Biolabs, and T4 DNA ligase and calf intestinal alkaline phosphatase were obtained from Boehringer-Mannheim.

EXAMPLE 1

Construction of Recombinant Plasmids Containing the gag-pol Region of Simian Immunodeficiency Virus (SIV)

Figure 2:
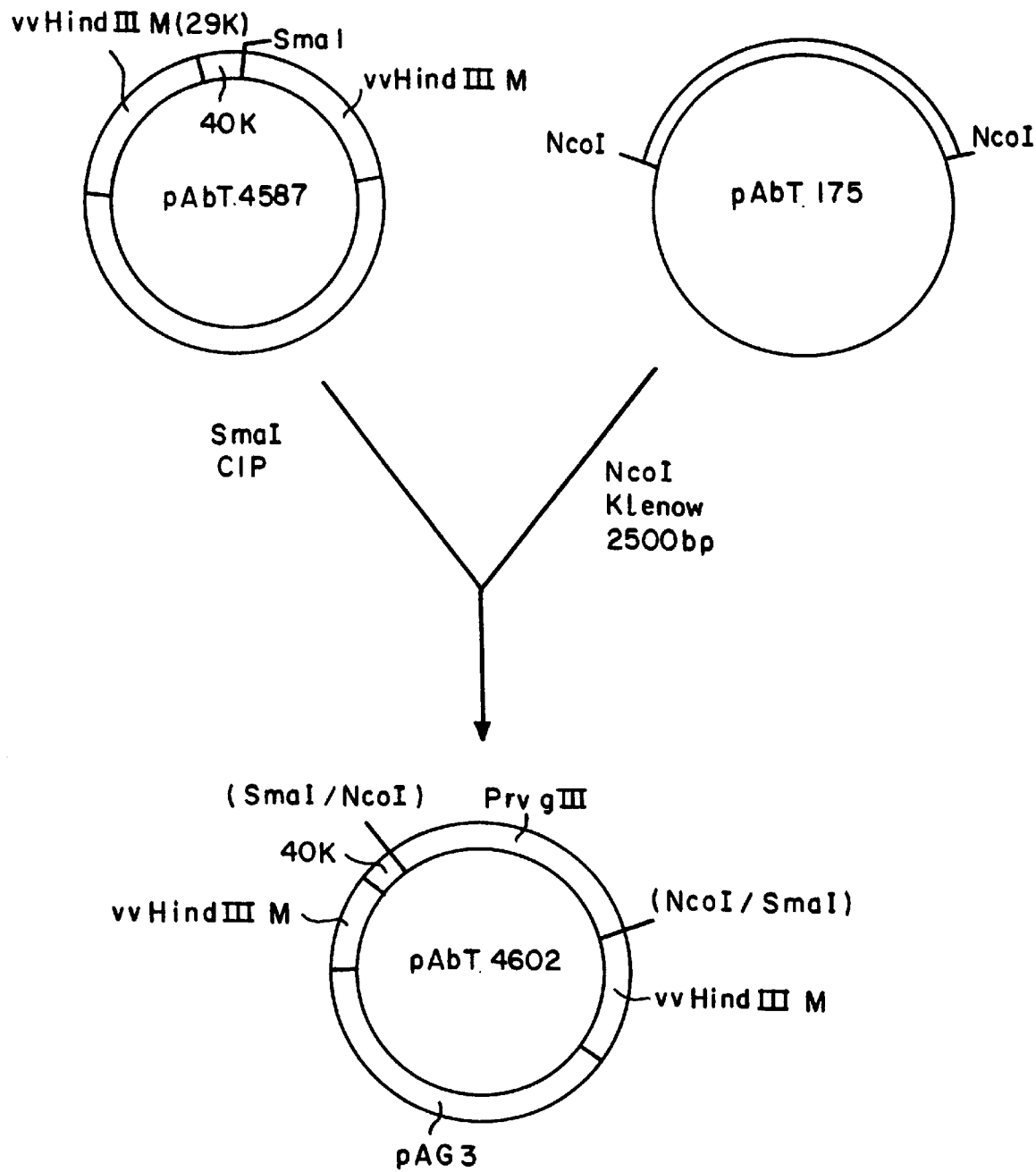

This example illustrates the construction of a recombinant plasmid containing SIV genes for in vivo recombination with vaccinia virus (IVR vector). The construction and structure of plasmids pAbT4579 is described in PCT Application No. WO89/12095, published Dec. 14, 1989. The construction and structure of plasmids pAbT4592 and pAbT4593 are described in U.S. patent application Ser. No. 360,027 filed Jun. 1, 1989. The teachings of these Applications are incorporated herein by reference.

a. Construction of pAbT4660 (FIG. 1).

Plasmid pAbT4592 was partially digested with HindIII, then digested to completion with SacI. An approximately 4990 base pair (bp) fragment containing a bacterial replicon, vaccinia sequences for integration into the HindIII M region of the genome, the vaccinia 40K promoter and the SIV gag gene was isolated. This fragment was ligated to a 3780 bp fragment resulting after digestion of plasmid pAbT4579 to completion with HindIII and SacI, to yield plasmid pAbT4660. pAbT4660 contains the entire SIV gag-pol region under the transcriptional direction of the vaccinia 40K promoter.

EXAMPLE 2

Construction of a Recombinant Plasmid Containing the gIII Gene of Pseudorabies Virus (PRV)

This example illustrates the construction of a recombinant plasmid containing the PRV gIII gene for in vivo recombination with vaccinia virus (IVR vector). The construction and structure of plasmid pAbT175 is described in EP 0261940, published Mar. 30, 1988. The construction and structure of plasmid pAbT4587 is described in PCT Application No. WO90/01546, published Feb. 22, 1990. The teachings of these Applications are incorporated herein by reference.

a. Construction of pAbT4602 (FIG. 2).

Plasmid pAbT175 was digested to isolate a 2500 bp NcoI fragment containing PRV gIII gene. The ends were repaired with the Klenow fragment of DNA polymerase I. This was ligated to vector pAbT4587 which had been digested with SmaI and treated with calf intestinal phosphatase. This situated the gIII gene downstream of the vaccinia virus 40K promoter to generate pAbT4602.

EXAMPLE 3

Construction of Recombinant Vaccinia Viruses Containing the SIV gag-pol Region or the PRV gIII Gene In vivo recombination is a method whereby recombinant vaccinia viruses are created (Nakano, et al., *Proc. Natl. Acad. Sci. USA*, 79:1593 (1982); Paoletti and Panicali, U.S. Pat. No. 4,603,112). These recombinant viruses are formed by transfecting DNA containing a gene of interest into cells which have been infected by vaccinia virus. A small percent of the progeny virus will contain the gene of interest integrated into a specific site on the vaccinia genome. These recombinant viruses can express genes of foreign origin. Panicali and Paoletti, *Proc. Natl. Acad. Sci. USA*, 79:4927 (1982); Panicali, et al., *Proc. Natl. Acad. Sci. USA*, 80:5364 (1983).

a. Insertion of SIV gag-pol Genes into Vaccinia Strain vAbT33

To insert SIV gag-pol genes into the vaccinia virus genome at the HindIII M region of vaccinia virus strain vAbT33, a selection scheme based upon the 29K host-range gene, which is located in this region, was used. Gillard, et al., *Proc. Natl. Acad. Sci. USA*, 83:5573 (1986). Recombinant vaccinia virus vAbT33 contains the lacZ gene in place of a portion of the 29K gene. This lacZ insertion destroys the function of the 29K gene; therefore, vAbT33 grows poorly on RK-13 cells, which require the 29K gene product. Furthermore, vAbT33 forms blue plaques on permissive cells in the presence of the chromogenic substrate for β-galactosidase, Bluogal™, due to the presence of the lacZ gene. See PCT Application No. WO89/12103, published Dec. 18, 1989.

IVR vector pAbT4660 was transfected into BSC-40 cells which had been infected with vaccinia virus vAbT33. Viral infection and plasmid transfection were performed essentially as described. Spyropoulos, et al., *J. Virol.*, 62:1046 (1988). Recombinant viruses were selected as white plaques in the presence of Bluogal™ on RK-13 cells. Plaques were picked and purified, and the final recombinant, designated vAbT394, was amplified.

b. Insertion of the PRV gIII Gene into Vaccinia Strain vAbT33.

To insert the PRV gIII gene into the vaccinia virus genome at the HindIII site of vaccinia virus, BSC-40 cells were infected with vAbT33, transfected with pAbT4602 and the recombinant selected by the scheme described in Example 3a. This generated vaccinia recombinant vAbT282.

c. Southern Blot Analysis of vAbT394 and vAbT282.

DNA was extracted from vaccinia virus-infected cells as described [Esposito, et al., *J. Virol. Methods*, 2:175 (1981)] and analyzed by restriction enzyme digestions and Southern hybridization with radiolabeled probes corresponding to the SIV gag-pol genes or PRV gIII gene as described. Maniatis, et al., *Molecular Cloning: Laboratory Manual*, Cold Spring Harbor Laboratory, Cold Spring Harbor, N.Y. (1982). This analysis confirmed the presence of these SIV and PRV sequences in the recombinant viruses.

EXAMPLE 4

Immunoprecipitation of SIV and PRV Antigens from Cells Infected with Recombinant Vaccinia Viruses Metabolic labeling with [$^{35}$S]-methionine of BSC-40 or RK-13 cells infected with either recombinant vaccinia viruses vAbT394 and vAbT282 and subsequent immunoprecipitation analyses were performed essentially as described in EP 0261940, published Mar. 30, 1988, the teachings of which are incorporated herein by reference. A monoclonal antibody designated M7 (Hampel, et al., *J. Virol.*, 52:583–590 (1984)) was used for immunoprecipitation of gIII expressed by vAbT282; IgG purified macaque anti-SIV antiserum was used for immunoprecipitation of the SIV proteins expressed by vAbT394. The results, which are summarized in Table 1, show that each of these vaccinia recombinants expresses the encoded polypeptide(s).

TABLE 1

| Immunoprecipitation of SIV and PRV polypeptides from recombinant vaccinia viruses | | |
|---|---|---|
| Vaccinia recombinants | Inserted genes | Proteins Observed |
| vAbT394 | SIV gag-pol | p66, p55, p42, p32, p27, p17, p10, p9 |
| vAbT292 | PRV gIII | gp76 |

EXAMPLE 5

Detection of Hybrid Retroviral Particles Produced by Coinfection with Vaccinia Recombinants vAbT282 and vAbT394

To demonstrate that vaccinia recombinant vAbT394 (SIV gag-pol) produces retroviral-like particles upon infection of mammalian cells, and to show that coinfection of mammalian cells with vAbT394 and vAbT282 (PRV gIII) results in the production of hybrid retroviral-like particles containing SIV core proteins and PRV gIII envelope glycoprotein, the following experiment was performed: BSC-40 cells were infected with vAbT394 and vAbT282 individually and in combination, in the presence of [$^{35}$S]-methionine as described in Example 3. After 16–18 hours of infection, the culture medium from each infection was collected and clarified by centrifugation twice at 3000 rpm for 5 minutes. The clarified media were then centrifuged at 25,000 rpm for 90 minutes. After removal of the supernatants, the resulting pellets were each resuspended in 400 μl of IP buffer (10 mM Tris pH 7.2, 0.5 mM NaCl, 1% Triton X-100, 1% NaDOC, 0.1% SDS, 5 mM EDTA, 100 mM PMSF, 10 mg/ml soybean trypsin inhibitor). Each of the three pellet samples were then subjected to immunoprecipitation analysis using macaque anti-SIV antibody and anti-PRV gIII monoclonal antibody M7 as described in Example 4. The results are shown in Table 2.

TABLE 2

Immunoprecipitation of SIV and PRV polypeptides from virus-like particles released into the medium of cells infected with vAbT394 and/or vAbT282

| Infecting virus(es) | Antibody used | Proteins Observed |
| --- | --- | --- |
| vAbT394 (SIV gag-pol) | M7 | none |
| vAbT394 | macaque anti-SIV | p66, p55, p42, p32, p27, p17, p10, p9 |
| vAbT282 (PRV gIII) | M7 | gp76 (weak) |
| vAbT282 | macaque anti-SIV | none |
| vAbT394 + vAbT282 | M7 | gp76 |
| vAbT394 + vAbT282 | macaque anti-SIV | p66, p55, p42, p32, p27, p17, p10, p9 |

These results showed that vAbT394 produces structures containing gag and pol polypeptides that are released into the culture medium of infected cells and can be pelleted from the medium by high-speed centrifugation. These structures are likely to be retroviral-like particles. Additionally, coinfection of cells with vAbT394 and vAbT282 results in the production of extracellular structures that contain both SIV polypeptides and PRV gIII. The amount of gIII detected by immunoprecipitation of material pelleted from culture media was considerably higher when cells are coinfected with vAbT394 and vAbT282 than when cells were infected with vAbT282 alone. These results suggested that coinfection with the two recombinant vaccinia viruses resulted in the production of hybrid virus-like particles comprising an SIV core surrounded by a membrane containing PRV gIII glycoprotein molecules.

EXAMPLE 6

Detection of Hybrid Retroviral Particles Produced by Coinfection with Vaccinia Recombinants that Express SIV and PRV Antigens Using Sucrose Gradient Sedimentation and Radioimmuno-Precipitation To confirm the production of retroviral-like particles containing both SIV capsid polypeptides and PRV gIII glycoproteins from cells coinfected with vAbT282 and vAbT394, the following experiments were performed.

BSC-40 cells were coinfected with the recombinant vaccinia viruses vAbT282 and vAbT394 at a multiplicity of 10 plaque-forming units (pfu) of each recombinant per cell in the presence of [$^{35}$S]-methionine as described in Example 4. After 20–24 hours of infection, the culture medium was collected and clarified by centrifugation twice at 3000 rpm for 5 minutes. The clarified medium was then centrifuged at 25,000 rpm for 90 minutes to pellet the virus-like particles. The supernatant was removed and the resulting pellet was resuspended in 3 ml PBS buffer (136 mM NaCl, 2.7 mM KCl, 8.1 mM Na$_2$HPO$_4$, 1.5 mM KH$_2$PO$_4$). The resuspended pellet was applied to a 15–45% continuous sucrose density gradient and centrifuged for 90 minutes at 25,000 rpm in a SW28 rotor. Fractions were collected dropwise. Samples from each sucrose gradient fraction were subjected to immunoprecipitation analysis using macaque anti-SIV antiserum or mouse monoclonal anti-PRV gIII (M7) as described in Example 4. The immunoprecipitates were analyzed by SDS-PAGE and the protein bands visualized by scintillation autofluorography (Bonner and Laskey, *European Journal of Biochem.*, 46:83–88 (1974)). SIV-specific protein bands, including processed gag polypeptides, reverse transcriptase and endonuclease, co-sedimented in the gradient at a density expected for SIV particles. These results demonstrate that the pelleted material contains retrovirus-like particles, rather than simple aggregates of retroviral polypeptides. The fractions were also analyzed for the presence of PRV gIII. The results showed that the sucrose gradient fractions containing peak concentrations of gag-pol antigens also contained peak concentrations of the gIII antigen. These results strongly suggested that the recombinant vaccinia-produced gIII, gag and pol proteins self-assemble into hybrid retrovirus-like particles.

EXAMPLE 7

Construction of a Divalent Vaccinia Recombinant Expressing SIV gag-pol and Equine Herpesvirus-1 (EHV-1) gB Genes Under the Control of Vaccinia Promoters It is possible to produce hybrid viral particles from a single recombinant virus that expresses both the capsid polypeptides and a viral glycoprotein of interest. As an example, a recombinant vaccinia virus that contains the SIV gag-pol genes inserted at the HindIII M region of the genome (vAbT394) can be used as the parent for insertion of an envelope glycoprotein gene inserted in the thymidine kinase (TK) gene (in the HindIII J region of the genome) by in vivo recombination with an appropriate IVR vector. One IVR vector suitable for this purpose is pAbT817, the construction of which is described in PCT Application No. WO90/01546, published Feb. 22, 1990, the teachings of which are incorporated herein by reference. pAbT817 contains the equine herpesvirus-1 (EHV-1) glycoprotein B (gB) gene, under the control of the vaccinia 40K promoter, the vaccinia TK gene for directing recombination in vaccinia, the *E. coli* lacZ gene under the control of the vaccinia BamF promoter for selection of recombinants and a bacterial replicon and ampicillin-resistance gene for growth and selection in *E. coli*.

To generate a recombinant virus that co-expresses EHV-1 gB and SIV gag-pol, the IVR vector pAbT817 can be transfected into TK$^-$ host cells (Hul42TK$^-$) which have been infected with vAbT394. The desired recombinant, which will be TK$^-$ due to the insertion of foreign DNA into the vaccinia TK gene, can be selected using bromodeoxyuridine (BUdR), which is lethal for TK$^+$ virus but allows recombinant TK$^-$ virus to grow. In addition, the recombinant virus will contain the *E. coli* lacZ gene and express β-galactosidase. Thus, the recombinant virus can also be identified by its ability to form blue plaques in the presence of Bluogal™.

The formation of capsids in cells infected with this recombinant virus can be demonstrated essentially as described in the preceding examples. After infecting cells with the recombinant expressing both SIV gag-pol and EHV-1 gB proteins, the culture medium can be analyzed by sedimentation, immunoprecipitation and PAGE methods described herein to demonstrate the production of virus-like particles containing the EHV-1 gG glycoprotein and SIV capsid proteins.

EXAMPLE 8

Figure 3:
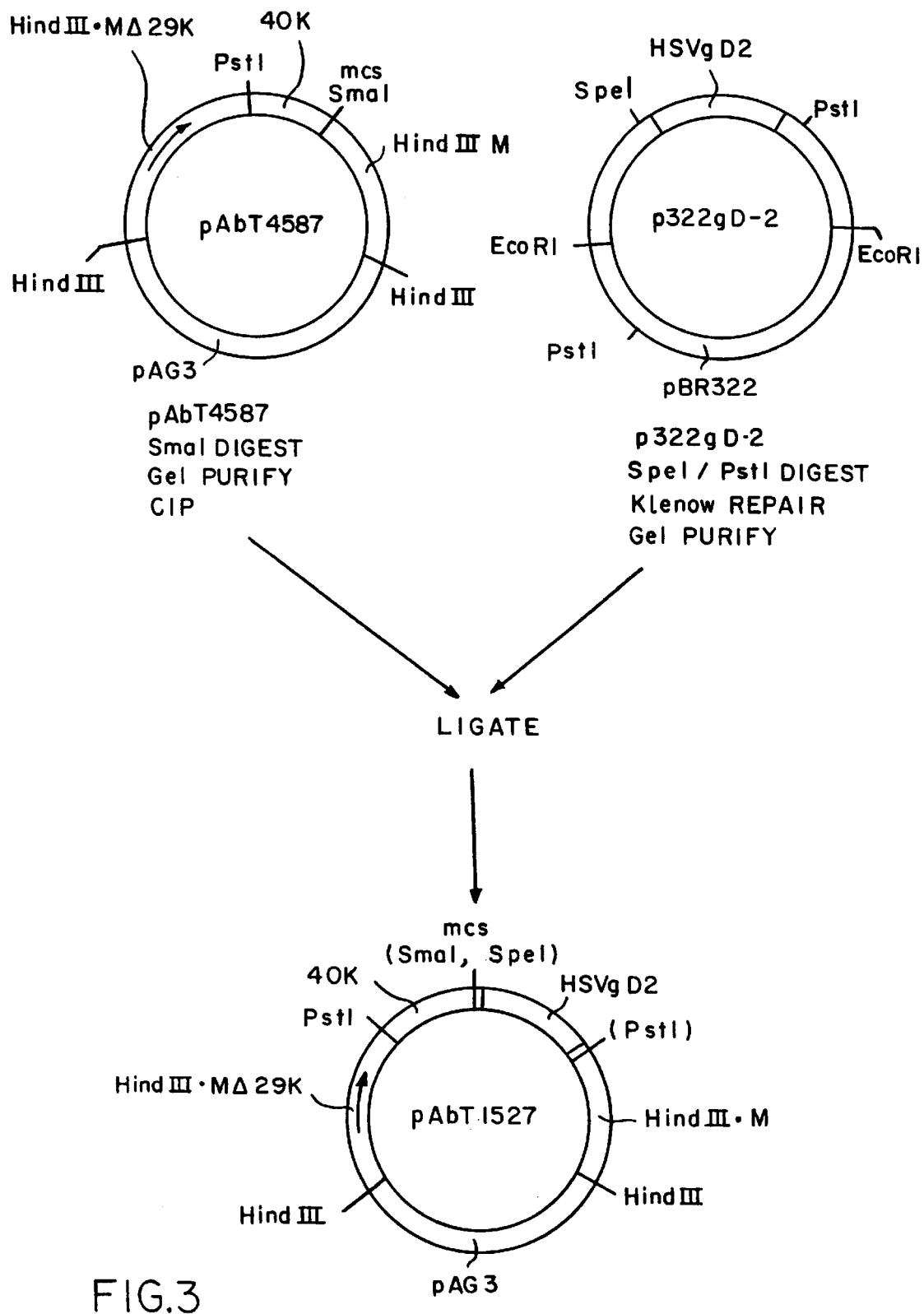

Construction of a Recombinant Plasmid Vector Containing the gD Gene of Herpes Simplex Virus Type 2 (HSV-2) (FIG. 3)

This Example illustrates the construction of recombinant plasmid vector containing the HSV-2 gD gene (gD2) for insertion into vaccinia virus.

Plasmid p322gD-2, which was obtained from Vickie Landolfi (Lederle-Praxis Biologicals, Pearl River, N.Y.) was digested with SpeI and PstI and treated with Klenow fragment of DNA polymerase I. The resulting 1400 bp fragment containing the gD2 gene was ligated to plasmid vector pAbT4587 (see, Example 2 above) which had been digested with SmaI and treated with calf intestinal phosphate, yielding plasmid pAbT1527. pAbT1527 contains the gD2 gene under the control of the vaccinia virus 40K promoter.

EXAMPLE 9

Construction of Recombinant Vaccinia Virus Containing the gD Gene of HSV-2

To insert the gD2 gene into the vaccinia virus genome at the HindIII M site of vaccinia virus, BSC-40 cells were infected with vAbT33, transfected with pAbT1527 and the recombinant virus selected and purified by the scheme described in Example 3a. This generated vaccinia recombinant vAbT509. To confirm the presence of the gD2 gene in the recombinant viral genome, DNA was extracted from vAbT509-infected cells and analyzed by restriction enzyme digestion with Southern hybridization, as described in Example 3c, using radiolabeled probes corresponding to the gD2 gene.

EXAMPLE 10

Immunoprecipitation of gD2 Antigen from Cells Infected with Recombinant Vaccinia Virus Immunoprecipitation analysis was carried out as described in Example 4, using vAbT509 and an anti-gD2 monoclonal antibody, designated DL6, obtained from Vickie Landolfi (Lederle-Praxis Biologicals, Pearl River, N.Y.). The results confirmed production of gD2 antigen in cells infected with vAbT509.

EXAMPLE 11

Detection of Hybrid Retroviral Particles Produced by Coinfection with Vaccinia Recombinants vAbT509 and vAbT394

To demonstrate that coinfection of mammalian cells with vAbT394 and vAbT509 (gD2) results in the production of hybrid retroviral-like particles containing SIV core proteins and HSV gD2 envelope glycoprotein, the following experiment was performed. Confluent BSC-40 cells were infected at a multiplicity of infection of 5 pfu/cell with either vAbT509 alone vAbT394 alone or vAbT509 and vAbT394 together. The culture media were harvested at 20 hours post-infection, and clarified by two ten-minute centrifugations at 3,000 rpm. The particulate material in each sample was then harvested by centrifugation at 120,000 g for 90 minutes in an SW28.1 rotor. The pelleted material from each sample was resuspended in 1.0 ml 10% glycerol in 10 mM Tris-HCl pH 7.2 and centrifuged at 120,000 g for 90 minutes in an SW28.1 rotor through a 15–45% linear sucrose gradient layered onto a 1.0 ml 60% sucrose cushion. The sucrose gradients were fractionated dropwise through the bottom of the tubes. The fractions were then chloroform/methanol precipitated and the samples were subjected to electrophoresis on a 12% SDS-polyacrylamide gel. The separated proteins were elctrophoretically transferred to Millipore filters and the proteins reacted with either the gD2-specific monoclonal antibody DL6 or with macaque anti-SIV serum. The filter-bound antigen/antibody complexes were visualized by reaction with a secondary chemiluminescent antibody.

After sedimentation through the sucrose gradient, the gD2 in the pellet fraction from cells infected with vaccinia recombinant vAbT509 migrated near the top of the gradient; this glycoprotein is most likely associated with membrane fragments pelleted by the ultracentrifugation of the clarified medium. By contrast, a large proportion of the SIV polypeptides contained in the pellet fraction from cells infected with vAbT394 were located in gradient fractions corresponding to the expected density for lentivirus-like particles.

In contrast to the results obtained in the single infection, the majority of the gD2 contained in the pellet material from cells co-infected with vAbT509 and vAbT394 co-sedimented with the SIV polypeptides in gradient fractions corresponding to the density of SIV-like particles. These results indicate that pseudotyped virus-like particles, comprising SIV core proteins and HSV gD2 glycoprotein, were generated in cells co-infected with recombinant vaccinia viruses expressing these polypeptides.

EXAMPLE 12

Immunogenicity of gD2/SIV Virus-like Particles

A pseudotyped virus-like particles (VLP-gD2) preparation was prepared from supernatant media from 5 roller bottles of BSC-40 cell cultures ($5\times10^8$ cells) co-infected for 18 hours with vAbT394 and vAbT509 at a multiplicity of infection of 3 pfu/cell of each virus. The supernatant medium was clarified by centrifugation two times at 3,000 rpm for 10 minutes. The clarified supernatant was layered on top of a 25% sucrose cushion and centrifuged 90 minutes at 120,000 g in an SW28 rotor. The sediments were resuspended in 500 ul of PBS and treated with 0.8% formalin at 40° C. overnight. A 5 ul sample of this material was blind-passaged two times on BSC-40 cells without any visible signs of infection arising in the cell cultures. Six week old mice in groups of 5 were immunized with 250 ul of material by either the intramuscular (IM) or the subcutaneous (SC) routes. The immunogen (VLP-gD2) preparation used for IM immunization was aluminum phosphate precipitated whereas the material used for SC immunization was not aluminum phosphate precipitated. Three weeks later the mice were immunized again with the same amount of material, treated in the same way and given by the same route as for the primary immunization. Thus, each mouse was immunized with a total of 1/10 the material generated in the 5 roller bottle starting cell culture. Another 5 mice were immunized with $1\times10^7$ pfu of vAbT509 first by tail scarification (TS) and three weeks later by intranasal (IN) instillation. All mice were bled 2 weeks after the second immunization. Anti-vaccinia and anti-gD2 immune responses were determined by ELISA. The ELISA plates were coated with either a vaccinia cell lysate or an HSV gD2 antigen purified from HSV-2 infected cells. Titer is defined as the reciprocal of the dilution which achieves 50% of the maximum value for the positive control (mouse anti-vaccinia sera or monoclonal anti-gD2 DL6). Results are shown in Table 3.

TABLE 3

Immunogenicity of Pseudotyped Virus-like Particles

| Antigen | Route | Anti-vac Titer of 5 mice | Anti-gD2 Titer of 5 mice |
|---|---|---|---|
| None | — | <10 | <10 |
| live vAbT509 | TS, IN | 480 | 480 |
| | | 480 | 480 |
| | | 640 | 1280 |
| | | 960 | 1280 |
| | | 1280 | 1280 |
| VLP-gD2 | SC, SC | <10 | 10 |
| | | <10 | 10 |
| | | <10 | 80 |
| | | <10 | 120 |
| | | <10 | 160 |
| VLP-gD2 | IM, IM | <10 | 20 |
| | | <10 | 80 |
| | | <10 | 120 |
| | | <10 | 120 |
| | | <10 | 1920 |

Mice immunized with $1\times10^7$ pfu of live recombinant vAbT509 first by tail scarification and three weeks later by intranasal instillation generated antibodies against vaccinia antigens and the HSV gD2 antigen. In contrast, mice immunized by the subcutaneous or intramuscular routes with gD2/SIV pseudovirions developed antibodies against the gD2 glycoprotein but the antibody response against vaccinia was several orders of magnitude lower than in mice immunized with live vaccinia. Thus, both the gD2 glycoprotein expressed by the recombinant vaccinia virus during infection of mice with vAbT509 and gD2 glycoprotein recovered in the pellet fraction after co-infection with cells with vAbT394 and vAbT509 elicit antibodies that recognize the purified gD2 glycoprotein.

Plasmid Deposits

The plasmids pAbT4660 and pAbT4602 were placed on deposit, under provisions of the Budapest Treaty, at the American Type Culture Collection (ATCC) in Rockville, Md. on Aug. 8, 1990, 1990. The plasmids have been assigned ATCC Accession Nos. 40866 and 40865, respectively.

Plasmid pAbT1527 was deposited at the ATCC, under the provisions of the Budapest Treaty, on Aug. 9, 1991, and received Accession No. 75057.

Equivalents

Those skilled in the art will recognize, or be able to ascertain using no more than routine experimentation, many equivalents to the specific embodiments of the invention described herein. Such equivalents are intended to be encompassed by the following claims:

I claim:

1. Plasmid DNA vector pAbT4602, pAbT4660 or pAbT1527 having ATCC designation numbers 40865, 40866, and 75057, respectively.

2. A DNA donor vector for insertion of DNA encoding a viral capsid polypeptide and an envelope glycoprotein from a different virus specie that self assemble into a replication-defective, hybrid virus particle, into a recombinant DNA viral vector by in vivo recombination, comprising:

a) a prokaryotic origin of replication so that the vector can be amplified in a prokaryotic host;

b) a gene encoding a marker which allows selection of prokaryotic host cells that contain the vector;

c) a DNA sequence encoding a viral capsid polypeptide and at least one other DNA sequence from a different virus encoding viral envelope glycoproteins that self-assemble into a replication-defective, hybrid virus particle, each DNA sequence located adjacent to a transcriptional promoter; and d) DNA sequence homologous to the region of the DNA viral genome where the DNA sequences will be inserted flanking the construct of element c.

3. A method of producing a self-assembled replication-defective, hybrid virus particle, comprising infecting a eukaryotic cell with a DNA viral vector which coexpresses in eukaryotic cells, a heterologous gene encoding a viral capsid polypeptide and at least one gene encoding a viral envelope glycoprotein from a different virus than the viral capsid, wherein the encoded capsid polypeptide and envelope glycoprotein self assemble into the replication-defective, hybrid virus particle.

4. A method of producing a self-assembled replication-defective, hybrid virus particle, comprising coinfecting a eukaryotic cell with at least two DNA viral vectors of the same virus specie, a first vector expressing a heterologous gene encoding a capsid polypeptide and a second vector expressing a gene encoding a viral envelope glycoprotein, wherein the encoded capsid polypeptide and envelope glycoprotein self assemble into the hybrid virus particle.

5. The method of claim 4, wherein at least one of the genes encoding viral envelope glycoprotein or the gene encoding the viral capsid polypeptide is operably linked to an inducible promoter.

6. The method of claim 5, wherein the vector containing the inducible promoter is used to transform a cell.

7. The method of claim 5, wherein both the gene encoding the capsid polypeptide and the gene encoding the viral envelope glycoprotein are under the control of an inducible promoter.

* * * * *